United States Patent
Bouix-Peter

(10) Patent No.: US 9,981,952 B2
(45) Date of Patent: *May 29, 2018

(54) OXAZETIDINE DERIVATIVES, PROCESS FOR PREPARING THEM AND USE IN HUMAN MEDICINE AND IN COSMETICS

(71) Applicant: Galderma Research & Development, Biot (FR)

(72) Inventor: Claire Bouix-Peter, Vallauris (FR)

(73) Assignee: GALDERMA RESEARCH & DEVELOPMENT, Biot (FR)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/139,018

(22) Filed: Apr. 26, 2016

(65) Prior Publication Data

US 2016/0237065 A1    Aug. 18, 2016

Related U.S. Application Data

(62) Division of application No. 14/130,282, filed as application No. PCT/EP2012/062622 on Jun. 28, 2012, now Pat. No. 9,353,083.

(60) Provisional application No. 61/503,068, filed on Jun. 30, 2011.

(30) Foreign Application Priority Data

Nov. 2, 2011   (FR) ...................... 11 59911

(51) Int. Cl.
| | | |
|---|---|---|
| *C07D 403/12* | (2006.01) | |
| *A61K 31/4178* | (2006.01) | |
| *A61K 8/49* | (2006.01) | |
| *A61Q 19/00* | (2006.01) | |
| *A61Q 19/08* | (2006.01) | |
| *C07D 401/12* | (2006.01) | |
| *A61Q 5/00* | (2006.01) | |

(52) U.S. Cl.
CPC .............. *C07D 403/12* (2013.01); *A61K 8/49* (2013.01); *A61K 8/4946* (2013.01); *A61K 31/4178* (2013.01); *A61Q 5/00* (2013.01); *A61Q 19/00* (2013.01); *A61Q 19/08* (2013.01); *C07D 401/12* (2013.01)

(58) Field of Classification Search
CPC .................................................... C07D 403/12
See application file for complete search history.

(56) References Cited

U.S. PATENT DOCUMENTS

| | | | | |
|---|---|---|---|---|
| 8,871,187 B2 * | 10/2014 | Bouix-Peter | ......... | A61K 8/4906 424/70.1 |
| 9,630,949 B2 * | 4/2017 | Bouix-Peter et al. | ........................... | C07D 403/12 424/800 |

FOREIGN PATENT DOCUMENTS

| | | | | |
|---|---|---|---|---|
| WO | 2010/052253 A1 | 5/2010 | | |
| WO | WO 2010/052253 A1 * | 5/2010 | ......... | A61K 31/4178 |

OTHER PUBLICATIONS

Bens, G. "Sunscreens," Adv. Exp. Med. Biol., 2014, vol. 810, pp. 429-463, Abstract.
Philip et al., "Clofazimine-induced Hair Pigmentation," Int. J. Trichology, 2012, vol. 4, Issue 3, pp. 174-175.
International Search Report dated Aug. 7, 2012 by the European Patent Office as the International Searching Authority in corresponding International Patent Application No. PCT/EP2012/062622, 3 pages.

* cited by examiner

*Primary Examiner* — Amanda L Aguirre
(74) *Attorney, Agent, or Firm* — Dentons US LLP

(57) ABSTRACT

Compounds that are agonists of the MC1R receptor and that exhibit reduced toxicity relative to other compounds of the same class are described. These compounds can have the general formula (I) wherein: R1 represents a cyclopropylmethyl or a 4-hydroxybutyl group; R2 represents a hydrogen atom or a methyl group; and also the salts and enantiomers of the corresponding compounds of general formula (I). Also described, are methods for treating hypopigmentary pathologies and photosensitive dermatoses.

10 Claims, No Drawings

OXAZETIDINE DERIVATIVES, PROCESS FOR PREPARING THEM AND USE IN HUMAN MEDICINE AND IN COSMETICS

CROSS-REFERENCE TO PRIOR APPLICATIONS

This application is a divisional of U.S. application Ser. No. 14/130,282, filed, Dec. 30, 2013, which is a National Stage of PCT/EP2012/062622, filed Jun. 28, 2012, and designating the United States (published in English on Jan. 3, 2013, as WO 2013/001030 A1), which claims priority under 35 U.S.C. § 119 to U.S. Provisional Patent Application 61/503,068, filed Jun. 30, 2011, each hereby expressly incorporated by reference in its entirety and each assigned to the assignee hereof.

The present invention relates to the pharmaceutical field and in particular to the treatment of hypopigmentary pathologies and photosensitive dermatoses. More specifically, the invention relates to compounds that are agonists of the MC1R receptor and which exhibit reduced toxicity relative to the other compounds of the same class.

Melanocortins form the family of regulatory peptides that are synthesized via a post-translational process of the hormone propiomelanocortin (POMC-131 amino acids long). POMC leads to the production of three classes of hormone: melanocortins, the hormone adrenocorticotropin and various endorphins, for instance lignotropin (Cone et al., Recent Prog. Norm. Res., 51: 287-317, (1996); Cone et al., Ann. N.Y. Acad. Sc., 31: 342-363, (1993)).

MCRs have varied physiological roles. MC1R regulates the formation of melanin in the skin, and has a role in regulating the immune system. MC2R regulates the production of corticosteroids in the adrenal glands. The receptors MC3R and MC4R play a role in controlling food intake and sexual behavior. MC5R is involved in regulating the exocrine glands (Wikberg, Jarl E. S., Melanocortin receptors: perspectives for novel drugs. European Journal of Pharmacology (1999), 375(1-3), 295-310. Wikberg, Jarl E. S. Melanocortin receptors: new opportunities in drug discovery. Expert Opinion on Therapeutic Patents (2001), 11(1), 61-76).

The potential use of MCRs as targets for medicaments for treating major pathologies such as obesity, diabetes, inflammatory conditions and sexual dysfunction raises the need for compounds that show high specificity towards a particular subtype. However, the modeling of selective medicaments, for slightly different receptor subtypes, is a difficult task that would be simplified if detailed knowledge regarding the determinants of the ligand-receptor interaction is known.

The Applicant has now found, surprisingly and unexpectedly, that novel compounds of general formula (I) as defined hereinbelow show very good activity on the melanocortin receptors and in particular are highly selective for MC1R and exhibit reduced toxicity relative to the other compounds of the same class.

Many MC1R agonists such as those described, for example, in patent WO 2010/52253, although being very active on the human receptor hMC1R, cannot be envisaged as molecules for progressing to clinical trials in man or as active principles of medicaments due to an alert regarding potential cardiotoxicity problems revealed in an in vitro test known as the hERG channel (Sanguinetti M C, Tristani-Firouzi M (March 2006). "hERG potassium channels and cardiac arrhythmia". Nature 440 (7083): 463-9).

Medicaments that prolong cardiac repolarization have been associated with a potentially mortal polymorphic ventricular tachycardia known as twisting spikes (TS).

In addition, several in vivo studies have shown that an increasing number of molecules of non-cardiovascular target are the cause of the potential risk of lengthening of the QT time, and that they might also cause "twisting spikes".

Almost all the medicaments known for exerting adverse cardiac effects (lengthening of the QT time, twisting spikes) in man have been reported also to block the hERG cardiac potassium channel. The human hERG (for human Ether-a-go-go related gene) channel is a six-segment transmembrane channel in the heart. It controls the IKr current and rapidly becomes inactivated (C-terminal inactivation).

Surprisingly, the Applicant has identified a sub-family of compounds corresponding to the general structure (I) described in WO 2010/52253, the compounds of which are highly active on the hMC1R receptor and do not present any cardiotoxic alert on the hERG channel test, unlike the other molecules included in that same patent. Specifically, there is a theoretical risk of side effects associated with the activity of MC4Rs present in the SNC (perturbation of food consumption, etc.).

These compounds find applications in human medicine, especially in dermatology, and in the cosmetics field.

Thus, the present invention relates to compounds of general formula (I) below:

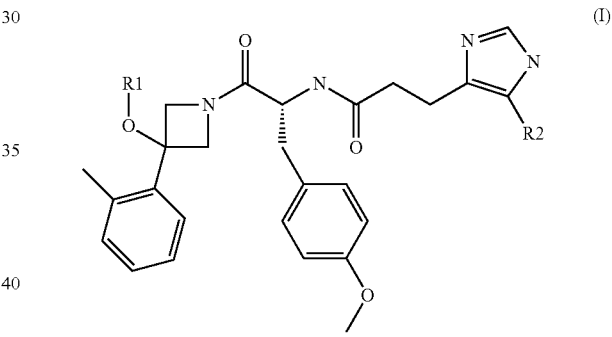

in which:
R1 represents a cyclopropylmethyl or a 4-hydroxybutyl group;
R2 represents a hydrogen atom or a methyl group.

The present invention preferably relates to the following compounds:
N—[(R)-2-[3-(4-hydroxybutoxy)-3-o-tolylazetidin-1-yl]-1-(4-methoxybenzyl-)-2-oxoethyl]-3-(-1H-imidazol-4-yl) propionamide.
N—[(R)-2-(3-cyclopropylmethoxy-3-o-tolylazetidin-1-yl)-1-(4-methoxybenzyl)-2-oxoethyl]-3-(5-methyl-1H-imidazol-4-yl)propionamide and also to the salts and enantiomers of the corresponding compounds of general formula (I).

Among the addition salts of the compounds of general formula (I) with a pharmaceutically acceptable acid, mention may preferably be made of the salts with an organic acid or with an inorganic acid.

The suitable mineral acids are, for example, hydrohalic acids, for instance hydrochloric acid or hydrobromic acid, sulfuric acid and nitric acid.

The appropriate organic acids are, for example, picric acid, methanesulfonic acid, ethanesulfonic acid, paratoluenesulfonic acid, citric acid, oxalic acid and tartaric acid.

The compounds of general formula (I) may also exist in the form of hydrates or solvates with water or with a solvent.

The suitable solvents for forming solvates or hydrates are, for example, alcohols, for instance ethanol or isopropanol, or water.

The invention is thus directed towards the use of at least one compound of general formula (I) as defined above for the preparation of a pharmaceutical or cosmetic composition in which the said compound has modulatory activity on one or more melanocortin receptors and in particular on the subtypes 1, 3, 4 and 5.

In one particular mode of the invention, the compounds of general formula (I) in the present invention have selective activity on the MC1R receptor and are particularly useful for treating pigmentary disorders and inflammatory and immune disorders.

The invention also relates to a therapeutic or cosmetic treatment method, comprising the administration of a pharmaceutical or cosmetic composition comprising the said compound, as modulators of one or more melanocortin receptors and in particular of the subtypes 1, 3, 4 and 5. In one particular mode, the invention also relates to a therapeutic or cosmetic method, comprising the administration of a pharmaceutical or cosmetic composition comprising the said compound, for treating pigmentary disorders or inflammatory and immune disorders. In one particular mode of the invention, the compounds are selective modulators of the subtype 1.

The invention also relates to the use of a compound of general formula (I) as defined above, for the preparation of a medicament for treating disorders associated with a dysfunction of the MC1R receptor.

Specifically, the compounds used according to the invention are particularly suitable for treating and/or preventing disorders and/or diseases selected from:

inflammatory diseases of the digestive apparatus, especially including the intestine (and particularly the colon in the case of irritable bowel syndrome, ulcero-haemorrhagic rectocolitis or Crohn's disease); pancreatitis, hepatitis (acute and chronic), inflammatory bladder pathologies and gastritis;

inflammatory diseases of the locomotor apparatus, including rheumatoid arthritis, osteoarthritis, osteoporosis, traumatic arthritis, post-infection arthritis, muscular degeneration and dermatomyositis;

inflammatory diseases of the urogenital apparatus and especially glomerulonephritis;

inflammatory diseases of the cardiac apparatus and especially pericarditis and myocarditis and diseases including those for which inflammation is an underlying factor (such as atherosclerosis, transplant atherosclerosis, peripheral vascular diseases, inflammatory vascular diseases, intermittent claudication or limping, restenosis, strokes, transient ischaemic attacks, myocardial ischaemia and myocardial infarction), hypertension, hyperlipidaemia, coronary diseases, unstable angina (or angina pectoris), thrombosis, platelet aggregation induced by thrombin and/or the consequences of thrombosis and/or of the formation of atheroma plaques;

inflammatory diseases of the respiratory and ORL apparatus, especially including asthma, acute respiratory distress syndrome, hayfever, allergic rhinitis and chronic obstructive pulmonary disease, or allergies;

inflammatory diseases of the central nervous system and especially Alzheimer's disease and any other form of dementia, Parkinson's disease, Creutzfeldt-Jakob disease, multiple sclerosis and meningitis;

inflammatory diseases of the skin, and especially urticaria, scleroderma, contact dermatitis, atopic dermatitis, psoriasis, ichthyosis, acne and other forms of folliculitis, rosacea and alopecia;

autoimmune diseases and especially lupus erythematosus, thyroid complaints, autoimmune diseases of the adrenal glands and autoimmune gastritis, vitiligo and alopecia areata;

inflammations accompanying bacterial, viral or fungal infections, especially tuberculosis, septicaemia, fever, HIV, irrespective of the location of the infection, herpes, cytomegalovirus, and hepatites A, B and C;

transplant or graft rejections, such as of the kidney, liver, heart, lung, pancreas, bone marrow, cornea, intestine or skin (skin allograft, homograft or heterograft, etc.);

the treatment of pain, irrespective of its origin, such as post-operative pain, neuromuscular pain, headaches, cancer-related pain, dental pain or osteoarticular pain;

modulating pigmentation, for the treatment of:

diseases with pigmentation disorders and especially benign dermatoses such as vitiligo, albinism, melasma, lentigo, ephelides, melanocytic naevus and all post-inflammatory pigmentations; and also pigmented tumors such as melanomas and their local (permeation nodules), regional or systemic metastases;

photo-protection for the purpose of preventing:

the harmful effects of sunlight, such as actinic erythema, cutaneous ageing, skin cancer (spinocellular, basocellular and melanoma) and especially diseases that accelerate its occurrence (xeroderma pigmentosum, basocellular naevus syndrome and familial melanoma);

photodermatoses caused by exogenous photosensitizers and especially those caused by contact photosensitizers (for example furocoumarins, halogenated salicylanilides and derivatives, and local sulfamides and derivatives) or those caused by systemic photosensitizers (for example psoralenes, tetracyclines, sulfamides, phenothiazines, nalidixic acid and tricyclic antidepressants);

bouts or outbreaks of dermatosis with photosensitivity and especially light-aggravated dermatoses (for example lupus erythematosus, recurrent herpes, congenital poikilodermal or telangiectatic conditions with photosensitivity (Bloom's syndrome, Cockayne's syndrome or Rothmund-Thomson syndrome), actinic lichen planus, actinic granuloma, superficial disseminated actinic porokeratosis, acne rosacea, juvenile acne, bullous dermatosis, Darier's disease, lymphoma cutis, psoriasis, atopic dermatitis, contact eczema, Chronic Actinic Dermatosis (CAD), follicular mucinosis, erythema multiforme, fixed drug eruption, cutaneous lymphocytoma, reticular erythematous mucinosis, and melasma);

dermatoses with photosensitivity by deficiency of the protective system with anomalies of melanin formation or distribution (for example oculocutaneous albinism, phenylketonuria, hypopituitarism, vitiligo and piebaldism) and with deficiency of the DNA repair systems (for example xeroderma pigmentosum and Cockayne's syndrome), dermatoses with photosensitivity via metabolic anomalies, for instance cutaneous porphyria (for example tardive cutaneous porphyria, mixed porphyria, erythropoietic protoporphyria, congenital erythropoietic porphyria (Gunther's disease), and erythropoietic coproporphyria), pellagra or pellagroid erythema (for example pellagra, pellagroid erythemas and tryptophan metabolism disorders);

bouts or outbreaks of idiopathic photodermatoses and especially PMLE (polymorphic light eruption), benign summer light eruption, actinic prurigo, persistent photosensitizations (actinic reticuloid, remanent photosensitizations and photosensitive eczema), solar urticaria, hydroa vacciniforme, juvenile spring eruption and solar pruritus;

modifying the colour of the skin or head hair and bodily hair, and especially by tanning the skin by increasing melanin synthesis or bleaching it by interfering with melanin synthesis, but also by preventing the bleaching or greying of head hair or bodily hair (for example canities and piebaldism); and also modifying the colour of head hair and bodily hair in cosmetic indications;

modifying the sebaceous functions, and especially the treatment of:

hyperseborrhoea complaints and especially acne, seborrhoeic dermatitis, greasy skin and greasy hair, hyperseborrhoea in Parkinson's disease and epilepsy and hyperandrogenism;

complaints with reduction of sebaceous secretion and especially xerosis and all forms of dry skin;

benign or malignant proliferation of sebocytes and the sebaceous glands;

inflammatory complaints of the pilosebaceous follicles and especially acne, boils, anthrax and folliculitis;

neurodegenerative disorders, including depression, anxiety, compulsive disorders (such as compulsive obsessive disorders), neuroses, psychoses, insomnia and sleeping disorder, sleep apnea, and drug abuse;

male or female sexual dysfunctions; male sexual dysfunctions including, but not limited to, impotence, loss of libido and erectile dysfunction; female sexual dysfunctions including, but not limited to, sexual stimulation disorders or desire-related disorders, sexual receptivity, orgasm, and disturbances of the major points of sexual function; pain, premature labor, dysmenorrhea, excessive menstruation, and endometriosis;

disorders related to weight but not limited to obesity and anorexia (such as modification or impairment of appetite, metabolism of the spleen, or the vocable irreproachable taking of fat or carbohydrates); diabetes mellitus (by tolerance to glucose doses and/or reduction of insulin resistance);

cancer and in particular lung cancer, prostate cancer, bowel cancer, breast cancer, ovarian cancer, bone cancer or angiogenesis disorders including the formation or growth of solid tumours.

Preferentially, the compounds according to the invention may also be used for treating and/or preventing disorders and/or diseases selected from:

skin diseases and especially urticaria, scleroderma, contact dermatitis, atopic dermatitis, psoriasis, ichthyosis, acne and other forms of folliculitis, rosacea and alopecia;

autoimmune diseases and especially lupus erythematosus, thyroid complaints, autoimmune diseases of the adrenal glands and autoimmune gastritis, vitiligo and alopecia areata;

diseases with pigmentation disorders and especially benign dermatoses such as vitiligo, albinism, melasma, lentigo, ephelides, melanocytic naevus and all post-inflammatory pigmentations; and also pigmented tumours such as melanomas and their local (permeation nodules), regional or systemic metastases;

photo-protection for the purpose of preventing:

the harmful effects of sunlight, such as actinic erythema, cutaneous ageing, skin cancer (spinocellular, basocellular and melanoma) and especially diseases that accelerate its occurrence (xeroderma pigmentosum, basocellular naevus syndrome and familial melanoma);

photodermatoses caused by exogenous photosensitizers and especially those caused by contact photosensitizers (for example furocoumarins, halogenated salicylanilides and derivatives, and local sulfamides and derivatives) or those caused by systemic photosensitizers (for example psoralenes, tetracyclines, sulfamides, phenothiazines, nalidixic acid and tricyclic antidepressants);

bouts or outbreaks of dermatosis with photosensitivity and especially light-aggravated dermatoses (for example lupus erythematosus, recurrent herpes, congenital poikilodermal or telangiectatic conditions with photosensitivity (Bloom's syndrome, Cockayne's syndrome or Rothmund-Thomson syndrome), actinic lichen planus, actinic granuloma, superficial disseminated actinic porokeratosis, acne rosacea, juvenile acne, bullous dermatosis, Darier's disease, lymphoma cutis, psoriasis, atopic dermatitis, contact eczema, follicular mucinosis, erythema multiforme, fixed drug eruption, cutaneous lymphocytoma, reticular erythematous mucinosis, and melasma);

dermatoses with photosensitivity by deficiency of the protective system with anomalies of melanin formation or distribution (for example oculocutaneous albinism, phenylketonuria, hypopituitarism, vitiligo and piebaldism) and with deficiency of the DNA repair systems (for example xeroderma pigmentosum and Cockayne's syndrome), dermatoses with photosensitivity via metabolic anomalies, for instance cutaneous porphyria (for example tardive cutaneous porphyria, mixed porphyria, erythropoietic protoporphyria, congenital erythropoietic porphyria (Gunther's disease), and erythropoietic coproporphyria), pellagra or pellagroid erythema (for example pellagra, pellagroid erythemas and tryptophan metabolism disorders);

bouts or outbreaks of idiopathic photodermatoses and especially PMLE (polymorphic light eruption), benign summer light eruption, actinic prurigo, persistent photosensitizations (actinic reticuloid, remanent photosensitizations and photosensitive eczema), solar urticaria, hydroa vacciniforme, juvenile spring eruption and solar pruritus;

modifying the color of the skin or head hair and bodily hair, and especially by tanning the skin by increasing melanin synthesis or bleaching it by interfering with melanin synthesis, but also by preventing the bleaching or greying of head hair or bodily hair (for example canities and piebaldism);

modifying the color of head hair and bodily hair in cosmetic indications.

Preferably, the compounds according to the invention are used for treating and/or preventing disorders and/or diseases selected from:

diseases with pigmentation disorders and especially benign dermatoses such as vitiligo, albinism, melasma, lentigo, ephelides, melanocytic naevus and all post-inflammatory pigmentations; and also pigmented tumors such as melanomas and their local (permeation nodules), regional or systemic metastases;

antisun protection for the purpose of preventing:

the harmful effects of sunlight, such as actinic erythema, cutaneous ageing, skin cancer (spinocellular, basocellular and melanoma) and especially diseases that accelerate its occurrence (xeroderma pigmentosum, basocellular naevus syndrome and familial melanoma);

photodermatoses caused by exogenous photosensitizers and especially those caused by contact photosensitizers (for example furocoumarins, halogenated salicylanilides and derivatives, and local sulfamides and derivatives) or those caused by systemic photosensitizers (for example psoralenes, tetracyclines, sulfamides, phenothiazines, nalidixic acid and tricyclic antidepressants);

bouts or outbreaks of dermatosis with photosensitivity and especially:

light-aggravated dermatoses (for example lupus erythematosus, recurrent herpes, congenital poikilodermal or telangiectatic conditions with photosensitivity (Bloom's syndrome, Cockayne's syndrome or Rothmund-Thomson syndrome), actinic lichen planus, actinic granuloma, superficial disseminated actinic porokeratosis, acne rosacea, juvenile acne, bullous dermatosis, Darier's disease, lymphoma cutis, psoriasis, atopic dermatitis, contact eczema, follicular mucinosis, erythema multiforme, fixed drug eruption, cutaneous lymphocytoma, reticular erythematous mucinosis, and melasma);

dermatoses with photosensitivity by deficiency of the protective system with anomalies of melanin formation or distribution (for example oculocutaneous albinism, phenylketonuria, hypopituitarism, vitiligo and piebaldism) and with deficiency of the DNA repair systems (for example xeroderma pigmentosum and Cockayne's syndrome), dermatoses with photosensitivity via metabolic anomalies, for instance cutaneous porphyria (for example tardive cutaneous porphyria, mixed porphyria, erythropoietic protoporphyria, congenital erythropoietic porphyria (Gunther's disease), and erythropoietic coproporphyria), pellagra or pellagroid erythema (for example pellagra, pellagroid erythemas and tryptophan metabolism disorders);

bouts or outbreaks of idiopathic photodermatoses and especially PMLE (polymorphic light eruption), benign summer light eruption, actinic prurigo, persistent photosensitizations (actinic reticuloid, remanent photosensitizations and photosensitive eczema), solar urticaria, hydroa vacciniforme, juvenile spring eruption and solar pruritus.

Alternatively, they are used for treating and/or preventing disorders chosen from:

skin diseases and especially urticaria, scleroderma, contact dermatitis, atopic dermatitis, psoriasis, ichthyosis, acne and other forms of folliculitis, rosacea and alopecia.

The compounds of formula (I) may also be used for preventing and/or treating the signs of ageing and/or the skin or for body or hair hygiene.

The present invention also relates to the use of the selected compounds, which are MC1R agonists, for treating diseases involving a hypopigmentation problem (e.g.: vitiligo).

A subject of the present invention is also a cosmetic or pharmaceutical composition intended in particular for the treatment of the abovementioned conditions, and which is characterized in that it comprises, in a pharmaceutically acceptable support that is compatible with the method of administration selected for this composition, a compound of general formula (I) in the form of one of its enantiomers or one of its salts with a pharmaceutically acceptable acid. The term "pharmaceutically acceptable support" means a medium that is compatible with the skin, mucous membranes and the integuments.

The administration of the composition according to the invention may be performed orally, enterally, parenterally, topically or ocularly. Preferably, the cosmetic or pharmaceutical composition is conditioned in a form that is suitable for topical application.

Via the oral route, the composition may be in the form of tablets, gel capsules, coated tablets, syrups, suspensions, solutions, powders, granules, emulsions, suspensions, or microspheres, nanospheres or lipid or polymeric vesicles allowing controlled release. Via the parenteral route, the composition may be in the form of solutions or suspensions for perfusion or for injection.

The compounds according to the invention are generally administered orally or systemically at a daily dose of about 0.01 mg/kg to 100 mg/kg of body weight, in 1 or more dosage intakes.

The compounds are used systemically at a concentration generally of between 0.001% and 10% by weight and preferably between 0.01% and 1% by weight relative to the weight of the composition.

Via the topical route, the pharmaceutical composition according to the invention is more particularly intended for treating the skin and mucous membranes, and may be in liquid, pasty or solid form, and more particularly in the form of ointments, creams, milks, emulsions, lotions, pomades, powders, impregnated pads, syndets, solutions, gels, sprays, foams, suspensions, sticks, shampoos or washing bases. They may also be in the form of suspensions of microspheres or nanospheres or lipid or polymeric vesicles or of polymeric or gelled patches allowing controlled release.

The compositions used for topical application have a concentration of compound according to the invention generally of between 0.001% and 10% by weight and preferably between 0.01% and 5% by weight relative to the total weight of the composition.

The compounds of general formula (I) according to the invention also find an application in the cosmetic field, in particular in protecting against the harmful aspects of sunlight, for preventing and/or combating photoinduced or chronological ageing of the skin and the integuments. Preferably, the compound(s) of general formula (I) have a concentration of between 0.001% and 5% by weight, relative to the total weight of the composition.

A subject of the invention is thus also a composition comprising, in a cosmetically acceptable support, at least one of the compounds of general formula (I). The term "cosmetically acceptable medium" means a medium that is compatible with the skin, mucous membranes and the integuments.

A subject of the invention is also the cosmetic use of a composition comprising at least one compound of general formula (I), for preventing and/or treating the signs of ageing and/or the skin.

A subject of the invention is also the cosmetic use of a composition comprising at least one compound of general formula (I) for body or hair hygiene.

The pharmaceutical and cosmetic compositions as described previously may also contain inert or even pharmacodynamically active additives as regards the pharmaceutical compositions, or combinations of these additives, and especially:

- wetting agents;
- flavor enhancers;
- preserving agents such as para-hydroxybenzoic acid esters;
- stabilizers;
- humidity regulators;
- pH regulators;
- osmotic pressure modifiers;
- emulsifiers;
- UV-A and UV-B screening agents;
- antioxidants, such as .alpha.-tocopherol, butylhydroxyanisole or butylhydroxytoluene, superoxide dismutase or ubiquinol;
- emollients;
- moisturizers, for instance glycerol, PEG-400, thiamorpholinone and derivatives thereof, or urea;
- antiseborrhoeic or antiacne agents, such as S-carboxymethylcysteine, S-benzylcysteamine, salts thereof or derivatives thereof, or benzoyl peroxide.

Needless to say, a person skilled in the art will take care to select the optional compound(s) to be added to these compositions such that the advantageous properties intrinsically associated with the present invention are not, or are not substantially, adversely affected by the envisaged addition.

Several examples of production of compounds of general formula (I) according to the invention and biological results will now be given, by way of illustration and with no limiting nature.

EXAMPLES

Example 1

Synthesis of N—[(R)2-(3-cyclopropylmethoxy-3-o-tolylazetidin-1-yl)-1-(4-methoxybenzyl-)-2-oxo-ethyl]-3-(5-methyl-1H-imidazol-4-yl)propionamide tert-Butyl 3-hydroxy-3-o-tolylazetidine-1-carboxylate 60 ml of a 1M solution of o-tolylmagnesium chloride in tetrahydrofuran are added dropwise to a solution, precooled to −78° C., of 7.4 g (42.8 mmol) of tert-butyl 3-oxazetidine-1-carboxylate in 60 ml of tetrahydrofuran. After stirring at −78° C. for 1 hour 30 minutes, the reaction medium is hydrolysed with 200 ml of saturated aqueous ammonium chloride solution and extracted with 150 ml of ethyl acetate. The organic phase is dried over sodium sulfate, filtered, and concentrated under vacuum. 12 g of crude residue are obtained and are purified on silica gel eluted with a heptane/ethyl acetate mixture, the polarity being increased from 90/10 to 50/50. 8.9 g (79%) of tert-butyl 3-hydroxy-3-o-tolylazetidine-1-carboxylate are obtained in the form of a white solid.

tert-Butyl 3-cyclopropylmethoxy-3-o-tolylazetidine-1-carboxylate 3 g (11.4 mmol) of tert-butyl 3-hydroxy-3-o-tolylazetidine-1-carboxylate in 20 ml of N,N-dimethylformamide are added dropwise to a suspension of 1.4 g of sodium hydride at 60% in oil (34.2 mmol) in 14 ml of N,N-dimethylformamide, precooled to 0° C. After stirring for 20 minutes, 1 ml of bromomethylcyclopropane (11.4 mmol) is added and stirring is continued for 1 hour 30 minutes. The reaction medium is hydrolysed with saturated aqueous ammonium chloride solution and then extracted with a 1/1 heptane/ethyl acetate mixture. The organic phase is washed with saturated aqueous sodium chloride solution, dried over sodium sulfate, filtered and concentrated under vacuum. 4 g of crude residue are obtained and are purified by chromatography on silica gel eluted with a heptane/ethyl acetate mixture, the polarity being increased from 95/5 to 80/20. 2.9 g (81%) of tert-butyl 3-cyclopropylmethoxy-3-o-tolylazetidine-1-carboxylate are obtained in the form of a yellow oil.

3-Cyclopropylmethoxy-3-o-tolylazetidine hydrochloride 2.8 g (9.0 mmol) of tert-butyl 3-cyclopropylmethoxy-3-o-tolylazetidine-1-carboxylate are placed in 40 ml of a 3M solution of hydrogen chloride in ethyl acetate and are stirred at room temperature for 1 hour 30 minutes. The reaction medium is concentrated under a stream of nitrogen and then taken up in a 50/50 heptane/ethyl acetate mixture and concentrated under vacuum. 2.2 g (96%) of 3-cyclopropylmethoxy-3-o-tolylazetidine hydrochloride are obtained in the form of a beige-colored solid.

tert-Butyl [(R)-2-(3-cyclopropylmethoxy-3-o-tolylazetidin-1-yl)-1-(4-methoxybenzyl)-2-oxoethyl] carbamate 1.9 g of 1-ethyl-3-(3-dimethylaminopropyl)carbodiimide hydrochloride (10.2 mmol), 1.4 g of N-hydroxybenzotriazole (10.2 mmol), 3.8 ml of triethylamine (27.2 mmol) and then 2.2 g (8.7 mmol) of 3-cyclopropylmethoxy-3-o-tolylazetidine hydrochloride dissolved in 35 ml of N,N-dimethylformamide are successively added to a solution of 2.7 g (9.2 mmol) of (R)-2-tert-butoxycarbonylamino-3-(4-methoxyphenyl)propanoic acid in 55 ml of N,N-dimethylformamide. The reaction medium is stirred at room temperature for 38 hours. A 1/1 heptane/ethyl acetate mixture is added and the reaction medium is washed with aqueous 1N sodium hydroxide solution. The organic phase is then washed with aqueous 1N hydrochloric acid solution, dried over sodium sulfate, filtered and concentrated under vacuum. 2.7 g of crude residue are obtained and are purified by chromatography on silica gel eluted with a heptane/ethyl acetate mixture, the polarity being increased from 95/5 to 60/40. 1.8 g (41%) of tert-butyl [(R)-2-(3-cyclopropylmethoxy-3-o-tolylazetidin-1-yl)-1-(4-methoxybenzyl)-2-oxoethyl]carbamate are obtained in the form of a white solid.

(R)-2-Amino-1-(3-cyclopropylmethoxy-3-o-tolylazetidin-1-yl)-3-(4-methoxyphenyl) propan-1-one hydrochloride 1.7 g (3.5 mmol) of tert-butyl [(R)-2-(3-cyclopropylmethoxy-3-o-tolylazetidin-1-yl)-1-(4-methoxybenzyl)-2- oxoethyl]carbamate are placed in 45 ml of a 3M solution of hydrogen chloride in ethyl acetate and are stirred at room temperature for 3 hours. After evaporation under a stream of nitrogen, the crude product is taken up in a mixture of heptane and ethyl acetate, and then concentrated under vacuum. 1.6 g (100%) of (R)-2-amino-1-(3-cyclopropylmethoxy-3-o-tolylazetidin-1-yl)-3-(4-methoxyphenyl) propan-1-one hydrochloride are obtained in the form of a beige-colored solid.

3-(5-Methyl-1H-imidazol-4-yl)propanoic acid hydrochloride 60 mg of 10% palladium-on-charcoal are introduced into a solution of 387 mg (2.1 mmol) of (E)-3-(5-methyl-1H-imidazol-4-yl)acrylic acid hydrochloride in 8 ml of 1/1 tetrahydrofuran/water, purged beforehand with nitrogen. The reaction medium is placed under a hydrogen atmosphere and then stirred for 19 hours. After filtering through Celite and rinsing thoroughly with dichloromethane, the recovered filtrate is concentrated under vacuum. The crude residue is taken up in toluene and concentrated again in order to remove the residual water, and is then taken up in a mixture of heptane and diisopropyl ether (80/20) with stirring for about 2 hours. The desired product precipitates and is filtered off under vacuum. 326 mg (83%) of 3-(5-methyl-1H-imidazol-4-yl)propanoic acid hydrochloride are obtained in the form of a white solid.

N-[2-(3-Cyclopropylmethoxy-3-o-tolylazetidin-1-yl)-1-(4-methoxybenzyl)-2-oxoethyl]-3-(5-methyl-1H-imidazol-4-yl)propionamide 389 mg (1.2 mmol) of O-(benzotriazol-1-yl)-N,N',N',N'-tetramethyluronium tetrafluoroborate and 0.5 ml of triethylamine (3.7 mmol) are added to a solution of 260 mg (1.4 mmol) of 3-(5-methyl-1H-imidazol-4-yl)propanoic acid hydrochloride in 4 ml of N,N-dimethylformamide. After 5 minutes, 402 mg (0.94 mmol) of (R)-2-amino-1-(3-cyclopropylmethoxy-3-o-tolylazetidin-1-yl)-3-(4-methoxyphenyl)propan-1-one hydrochloride dissolved in 4 ml of N,N-dimethylformamide are added. The reaction medium is stirred at room temperature for 72 hours, aqueous 1N sodium hydroxide solution is then added and the medium is extracted with 50 ml of a 1/1 heptane/ethyl acetate mixture. The organic phase is washed with saturated aqueous sodium chloride solution, dried over sodium sulfate, filtered and concentrated under vacuum. 110 mg of crude residue are obtained and are purified by chromatography on silica gel eluted with dichloromethane, the polarity then being increased up to a 90/10 dichloromethane/methanol mixture.

279 mg (56%) of N-[2-(3-cyclopropylmethoxy-3-o-tolylazetidin-1-yl)-1-(4-methoxybenzyl)-2-oxoethyl]-3-(5-methyl-1H-imidazol-4-yl)propionamide are obtained in the form of a white solid.

$^1$H NMR (DMSO, 400 MHz) at 100° C.: 1.74 (s, 3H); 2.06 (s, 3H); 2.21 (s, 3H); 2.30-2.45 (m, 2H); 2.55-2.70 (m, 2H); 2.74-3.10 (m, 2H); 3.55-3.80 (m, 5H); 4.00-4.45 (m, 4H); 4.50 (q, J=8.0 Hz, 1H); 6.65-6.85 (m, 2H); 7.00-7.15 (m, 2H); 7.15-7.35 (m, 5H); 7.75-7.90 (m, 1H).

Example 2

Synthesis of N—[(R)-2-[3-(4-hydroxybutoxy)-3-o-tolylazetidin-1-yl]-1-(4-methoxybenzyl-)-2-oxoethyl]-3-(1H-imidazol-4-yl)propionamide 2-1: tert-Butyl 3-(4-benzyloxybutoxy)-3-o-tolylazetidine-1-carboxylate 1 g (3.79 mmol) of tert-butyl 3-hydroxy-3-o-tolylazetidine-1-carboxylate dissolved in 5 ml of N,N-dimethylformamide is added dropwise to a suspension of 455 mg (11.4 mmol) of 60% sodium hydride in oil, precooled to 20° C. After stirring for 15 minutes, 2.77 g (11.4 mmol) of 4-benzyloxybutyl bromide are added and stirring is continued for 15 hours at room temperature. The reaction medium is hydrolysed with water and then extracted with ethyl acetate. The organic phase is washed three times with water, dried over sodium sulfate, filtered and concentrated under reduced pressure. The crude residue obtained is purified by chromatography on silica gel eluted with a heptane/ethyl acetate mixture, the polarity being increased from 100/0 to 90/00. 1.43 g of tert-butyl 3-(4-benzyloxybutoxy)-3-o-tolylazetidine-1-carboxylate are obtained in the form of a colourless oil in a yield of 80%.

2-2: 3-(4-Benzyloxybutoxy)-3-o-tolylazetidine trifluoroacetate 1.43 g (3.36 mmol) of tert-butyl 3-(4-benzyloxybutoxy)-3-o-tolylazetidine-1-carboxylate are dissolved in 10 ml of dichloromethane. 4 ml (52 mmol) of trifluoroacetic acid are added dropwise and the mixture is stirred at room temperature for 1 hour and then concentrated to dryness. 1.5 g of 3-(4-benzyloxybutoxy)-3-o-tolylazetidine trifluoroacetate are obtained in the form of a colorless oil in quantitative yield.

2-3: tert-Butyl [(R)-2-[3-(4-benzyloxybutoxy)-3-o-tolylazetidin-1-yl]-1-(4-methoxybenzyl)-2-oxoethyl]carbamate 778 mg (4 mmol) of 1-ethyl-3-(3-dimethylaminopropyl) carbodiimide hydrochloride and 544 mg (4 mmol) of N-hydroxybenzotriazole are successively added to a solution of 1 g (3.36 mmol) of (R)-2-tert-butoxycarbonylamino-3-(4-methoxyphenyl)propanoic acid dissolved in 10 ml of N,N-dimethylformamide. After stirring for 15 minutes, 1.5 g (3.36 mmol) of 3-(4-benzyloxybutoxy)-3-o-tolylazetidine trifluoroacetate are added and stirring is continued for 15 minutes at room temperature. 2.34 ml (13.4 mmol) of N,N-diisopropylethylamine are added and the mixture is stirred at room temperature for 2 hours. Aqueous 1N sodium hydroxide solution is added and the reaction medium is extracted twice with ethyl acetate. The organic phase is then washed with aqueous 1N sodium hydroxide and then with aqueous 1N hydrochloric acid solution, dried over magnesium sulfate, filtered and concentrated under reduced pressure. The crude residue obtained is purified by chromatography on silica gel eluted with a heptane/ethyl acetate mixture, the polarity being increased from 100/0 to 70/40. 1.14 g of tert-butyl [(R)-2-[3-(4-benzyloxybutoxy)-3-o-tolylazetidin-1-yl]-1-(4-methoxybenzyl)-2-oxoethyl]carbamate are obtained in the form of a colorless resin, in a yield of 53%.

2-4: 2-Amino-1-[3-(4-benzyloxybutoxy)-3-o-tolylazetidin-1-yl]-3-(4-methoxy-phenyl)propan-1-one trifluoroacetate 1.14 g (1.89 mmol) of tert-butyl [(R)-2-[3-(4-benzyloxybutoxy)-3-o-tolylazetidin-1-yl]-1-(4-methoxybenzyl)-2-oxoethyl]carbamate are dissolved in 10 ml of dichloromethane. 3 ml (39 mmol) of trifluoroacetic acid are added dropwise and the mixture is stirred at room temperature for 1 hour and then concentrated to dryness. 1.4 g of 2-amino-1-[3-(4-benzyloxybutoxy)-3-o-tolylazetidin-1-yl]-3-(4-methoxyphenyl) propan-1-one trifluoroacetate are obtained in the form of a colorless resin, in quantitative yield.

2-5: N—[(R)-2-[3-(4-Benzyloxybutoxy)-3-o-tolylazetidin-1-yl]-1-(4-methoxy-benzyl)-2-oxoethyl]-3-(1H-imidazol-4-yl)propionamide 910 mg (2.83 mmol) of O-(benzotriazol-1-yl)-N,N,N',N'-tetramethyluronium tetrafluoroborate and 0.8 ml (5.67 mmol) of triethylamine are added to a solution of 500 mg (1.89 mmol) of 3-(5-methyl-1H-imidazol-4-yl)propanoic acid hydrochloride in 5 ml of N,N-dimethylformamide. After 60 minutes, 1.4 g (1.89 mmol) of 2-amino-1-[-3-(4-benzyloxybutoxy)-3-o-tolylazetidin-1-yl]-3-(4-methoxyphenyl)propan-1-one trifluoroacetate dissolved in 5 ml of N,N-dimethylformamide are added. The reaction medium is stirred at room temperature for 72 hours, aqueous 1N sodium hydroxide solution is then added and the medium is extracted twice with 50 ml of a 2/8 heptane/ethyl acetate mixture. The organic phase is washed with aqueous 1N sodium hydroxide and then with aqueous 1N hydrochloric acid solution, dried over magnesium sulfate, filtered and concentrated under reduced pressure. The crude product obtained is purified by chromatography on silica gel eluted with a 90/10 dichloromethane/methanol mixture. 1 g of N—[(R)-2-[3-(4-benzyloxybutoxy)-3-o-tolylazetidin-1-yl]-1-(4-methoxybenz-yl)-2-oxoethyl]-3-(1H-imidazol-4-yl)propionamide is obtained in the form of a white solid, in a yield of 84%.

2-6: N—[(R)-2-[3-(4-Hydroxybutoxy)-3-o-tolylazetidin-1-yl]-1-(4-methoxybenzyl)-2-oxoethyl]-3-(1H-imidazol-4-yl)propionamide 900 mg (1.44 mmol) of N—[(R)-2-[3-(4-benzyloxybutoxy)-3-o-tolylazetidin-1-yl]-1-(4-methoxybenz-yl)-2-oxoethyl]-3-(1H-imidazol-4-yl)propionamide are dissolved in 100 ml of acetic acid. 90 mg of 20% palladium hydroxide dispersed on active charcoal are added and the mixture is placed under a dihydrogen atmosphere and stirred for 1 hour at room temperature. The reaction medium is filtered through a layer of Celite and then concentrated to dryness. The crude residue obtained is purified by chromatography on silica gel eluted with an 85/15 dichloromethane/methanol mixture. 440 mg of N—[(R)-2-[3-(4-hydroxybutoxy)-3-o-tolylazetidin-1-yl]-1-(4-methoxybenzyl)-2-oxoethyl]-3-(1H-imidazol-4-yl)propionamide are obtained in the form of a white solid, in a yield of 67%.

$^1$H NMR (DMSO, 400 MHz) at 100° C.: 1.74 (s, 3H); 2.06 (s, 3H); 2.21 (s, 3H); 2.30-2.45 (m, 2H); 2.55-2.70 (m, 2H); 2.74-3.10 (m, 2H); 3.55-3.80 (m, 5H); 4.00-4.45 (m, 4H); 4.50 (q, J=8.0 Hz, 1H); 6.65-6.85 (m, 2H); 7.00-7.15 (m, 2H); 7.15-7.35 (m, 5H); 7.75-7.90 (m, 1H).

Example 3

Study of the Toxicity of the Compounds

This example describes a comparative study of toxicity of selected compounds.

The object of the study was to track down the inhibition profile of seven selective compounds from human cell lines stably transfected with the gene for expressing the IKr protein of the hERG potassium channel. Several MC1R agonist compounds and especially the compounds of interest in the context of the invention were evaluated. The toxicity evaluation was performed using three increasing concentrations (1, 3 and 10 μM) of 2 hERG transfected cells (no reference compound used) of the following compounds:

Compound 1: N—[(R)-2-[3-(4-hydroxybutoxy)-3-o-tolylazetidin-1-yl]-1-(4-methoxybenzyl-)-2-oxoethyl]-3-(1H-imidazol-4-yl)propionamide Compound 2: (S)—N—[(R)-2-(3-butoxy-3-o-tolylazetidin-1-yl)-1-(4-methoxybenzyl)-2-oxoethyl]-2-hydroxy-3-(1H-imidazol-4-yl)propionamide Compound 3: 3-(1H-imidazol-4-yl)-N—{(R)-1-(4-methoxybenzyl)-2-oxo-2-[3-o-tolyl-3-(4,4-,4-trifluorobutoxy)azetidin-1-yl]ethyl}propionamide Compound 4: N—[(R)-2-(3-but-2-ynyloxy-3-o-tolylazetidin-1-yl)-1-(4-methoxybenzyl)-2-oxoethyl]-3-(5-methyl-1H-imidazol-4-yl)propionamide Compound 5: N—[(R)-2-(3-cyclobutylmethoxy-3-o-tolylazetidin-1-yl)-1-(4-methoxybenzyl-)-2-oxoethyl]-3-(5-methyl-1H-imidazol-4-yl)propionamide Compound 6: N—[(R)-2-(3-cyclopropylmethoxy-3-o-tolylazetidin-1-yl)-1-(4-methoxybenzyl-l)-2-oxoethyl]-3-(5-methyl-1H-imidazol-4-yl)propionamide Compound 7: N—[(R)-2-(3-butoxy-3-o-tolylazetidin-1-yl)-1-(4-methoxybenzyl)-2-oxoethyl]-3-guanidinopropionamide; bis(trifluoroacetic acid) salt The effect on the amplitude of IKr encoded by hERG (as the changes in percentages relative to the control) are summarized per compound and per concentration in Table 1 below.

TABLE 1

|  | 1 μM | 3 μM | 10 μM | Estimated IC$_{50}$ for hERG channel blockade |
|---|---|---|---|---|
| Compound 1 | −1.5 ± 2.5 | −3.0 ± 1.0 | −7.5 ± 3.5 | — |
| Compound 2 | +1.0 ± 1.0 | −5.0 ± 5.0 | −51.5 ± 6.5 | 10 μM |
| Compound 3 | −16.0 ± 3.0 | −42.5 ± 5.5 | −86.5 ± 3.5 | >3 μM |
| Compound 4 | −20.5 ± 9.5 | −22.0 ± 10.0 | −42.5 ± 2.5 | >10 μM |
| Compound 5 | −17.0 ± 4.0 | −49.5 ± 16.5 | −76.5 ± 17.5 | 3 μM |
| Compound 6 | −5.0 ± 3.0 | −9.5 ± 3.5 | −16.0 ± 7.0 | — |
| Compound 7 | −19.5 ± 4.5 | −29.5 ± 9.5 | −33.0 ± 12.0 | >10 μM |

Compound 1: no effect observed on the amplitude of IKr

Compound 2: the amplitude of IKr was modified but only at the highest concentration (10 μM)

Compound 3: dose effect observed by decreasing the amplitude of IKr starting from 1 μM with an 86.5% decrease with 10 μM Compound 4: dose effect observed by decreasing the amplitude of IKr starting from 3 μM with a 42.5% decrease with 10 μM Compound 5: dose effect observed by decreasing the amplitude of IKr starting from 1 μM with a 76.5% decrease with 10 μM Compound 6: no effect observed on the amplitude of IKr Compound 7: slight dose effect observed by decreasing the amplitude of IKr starting from 1 μM with a 33% decrease with 10 μM

CONCLUSION

Under the experimental conditions, five of the seven compounds evaluated are responsible for lengthening the QT time, either slightly (compound 7) or more substantially (compounds 2, 3, 4 and 5). Conversely, only two compounds (compound 1 and compound 6) did not exhibit this characteristic.

This example shows that the selected compounds (compound 1: N—[(R)-2-[3-(4-hydroxybutoxy)-3-o-tolylazetidin-1-yl]-1-(4-methoxybenzyl-)-2-oxoethyl]-3-(1H-imidazol-4-yl)propionamide and compound 6: N—[(R)-2-(3-cyclopropylmethoxy-3-o-tolylazetidin-1-yl)-1-(4-methoxybenzyl)-2-oxoethyl]-3-(5-methyl-1H-imidazol-4-yl)propionamide) do not present any cardiotoxic alert on the hERG channel test, unlike other molecules, and thus show improved toxicity.

Example 4

Transactivation Test Melanocortin Receptors

The aim of this example is to show the Melanocortine receptor selectivity of compound 1 and compound 6 of the present invention:

Cells: The lines HEK293 are transfected with vectors pCRE-Luc and hMC1R or hMC4R. The cells are cultured at 37° C. and 5% $CO_2$, in DMEM medium supplemented with 10% foetal calf serum.

Test principle: In the presence of an activator (agonist), the melanocortin receptor will activate the cAMP pathway, which, via the vector CRE-Luc, will lead to the synthesis of luciferase. After addition of a lysis buffer containing a luminescent luciferase substrate, the luminescence proportional to the degree of activation or inhibition of receptor may be measured.

Testing the products: The products are dissolved at 10 mM in DMSO. They are tested as a response dose at 0.1% of DMSO final. The range comprising 10 points and a zero starts at 10 μM with four-fold dilutions. To test agonists, the products are tested alone. To determine the antagonist behavior, the products of interest are tested in the presence of 1 nM NDP-MSH (reference agonist). The cells are inoculated at a rate of 5000 cells per well (384-well plate) in serum-free DMEM medium and incubated overnight at 37° C. and 5% $CO_2$.

The products and the reference ligand (NDP-MSH) are added the following day and the plates are reincubated for 6 hours at 37° C. and 5% $CO_2$. After adding the lysis buffer containing luciferin, the plates are read in a Top-Count machine. The results are normalized as percentage of activity using the 100% (cells+NDP-MSH at 10 nM) and 0% (cells alone) controls. An EC50 is calculated for each product using the XLFit software. The results are given in nM and presented in the table below.

| Compound | EC50 hMC1-R (nM) | EC50 hMC4-R (nM) |
|---|---|---|
| Compound 1 | 250 | 8000 |
| Compound 6 | 70 | 4500 |

This example clearly shows that the compound 1 and the compound 6 are hMC1R highly selective.

What is claimed is:

1. A compound of general formula (I) below:

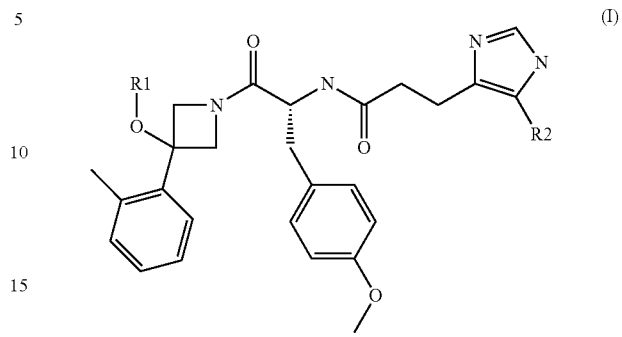

in which:
R1 represents a cyclopropylmethyl and R2 represents a methyl group; or
R1 represents a 4-hydroxybutyl group and R2 represents a hydrogen atom or a methyl group;
and also salts and enantiomers of the corresponding compounds of general formula (I).

2. The compound according to claim 1, wherein the compound of general formula (I) is selected from the group consisting of:
N—[(R)-2-[3-(4-hydroxybutoxy)-3-o-tolylazetidin-1-yl]-1-(4-methoxybenzyl)-2-oxoethyl]-3-(-1H-imidazol-4-yl)propionamide,
N—[(R)-2-(3-cyclopropylmethoxy-3-o-tolylazetidin-1-yl)-1-(4-methoxybenzy1)-2-oxoethyl]-3-(5-methyl-1H-imidazol-4-y1)propionamide,
and also corresponding salts and enantiomers.

3. The compound according to claim 1, wherein the compound is provided in a medicament.

4. A pharmaceutical composition comprising, in a physiologically acceptable medium, at least one compound of general formula (I) as defined in claim 1.

5. The composition according to claim 4, wherein the concentration of the compound of general formula (I) is between 0.001% and 10% by weight relative to the total weight of the composition.

6. The composition according to claim 4, wherein the concentration of the compound of general formula (I) for a topical application is between 0.01% and 5% by weight relative to the total weight of the composition.

7. A cosmetic composition comprising, in a cosmetically acceptable support, at least one compound of general formula (I) as defined in claim 1.

8. The composition according to claim 7, wherein the concentration of the compound of general formula (I) is between 0.001% and 3% by weight relative to the total weight of the composition.

9. A cosmetic method for treating signs of aging and/or treating skin, the method comprising administering the composition as defined in claim 7 to an individual subject in need thereof.

10. A cosmetic method for body or hair hygiene, the method comprising administering the composition as defined in claim 7 to an individual subject in need thereof.

* * * * *